United States Patent [19]

Takamura et al.

[11] Patent Number: 4,526,622
[45] Date of Patent: Jul. 2, 1985

[54] METHOD OF CLEANING ENDOSCOPE CHANNELS

[75] Inventors: Koji Takamura; Fumiaki Ishii; Yukio Nakajima; Hisao Yabe; Hiroyuki Sasa; Takeaki Nakamura, all of Tokyo, Japan

[73] Assignee: Olympus Optical Co., Ltd., Tokyo, Japan

[21] Appl. No.: 599,161

[22] Filed: Apr. 11, 1984

[30] Foreign Application Priority Data

Apr. 15, 1983 [JP]  Japan ............... 66798
Apr. 25, 1983 [JP]  Japan ............... 72521
Apr. 27, 1983 [JP]  Japan ............... 74773

[51] Int. Cl.³ ............... B08B 3/04; B08B 9/00
[52] U.S. Cl. ............... 134/21; 134/22.12; 134/22.18; 134/24; 134/34; 422/33
[58] Field of Search ............... 134/21, 22.12, 22.18, 134/24, 166 C, 169 C, 171, 34; 128/6; 239/106, 112; 422/28, 33

[56] References Cited

U.S. PATENT DOCUMENTS 2,993,494  7/1961  Svensson ............... 134/169 C
3,963,438  6/1976  Banez .
4,064,886  12/1977  Heckele ............... 134/171 X
4,216,767  8/1980  Aoshiro ............... 134/171 X
4,278,101  7/1981  Tanaka et al. ............... 134/171 X
4,281,646  8/1981  Kinoshita ............... 128/6
4,281,674  8/1981  Tanaka et al. ............... 134/171 X
4,288,882  9/1981  Takeuchi ............... 134/199 X
4,299,244  11/1981  Hirai ............... 134/171 X Primary Examiner—Marc L. Caroff

[57] ABSTRACT

In a method of cleaning the channels of an endoscope, one end of a suction channel and a nozzle, both positioned at the distal end of an insertion section of the endoscope, are connected. The open ends of an air/liquid supply cylinder and a suction valve cylinder, both provided within a control section of the endoscope, are closed. The ends of an air supply channel and a liquid supply channel, which open to a connector mounted on the distal end of a light guide cable, are connected to a liquid supply tube which is in contact with liquid. The other end of the suction channel, which opens to the connector, is connected to a suction pump by a suction tube. The pump is operated and sucks the liquid from the other end of the suction channel through the air supply channel, liquid supply channel, suction channel and valve cylinders, thereby cleaning the interior of the channels and valve cylinders with the liquid.

6 Claims, 6 Drawing Figures

METHOD OF CLEANING ENDOSCOPE CHANNELS

BACKGROUND OF THE INVENTION

The present invention relates to a method of cleaning various channels of an endoscope.

An endoscope generally has various channels for supplying or drawing by suction air or liquids. Therefore, when a used endoscope is to be cleaned, not only the outer surface thereof but also the channel interiors must be cleaned. The word "cleaning" used herein includes the steps of water cleaning for removing contaminants in the channels, disinfection with a disinfectant after such water washing, and then water washing after disinfection. These cleaning steps are usually performed in the order named above. However, in a conventional method of cleaning the channel interiors, a cleaning solution injection tube must be inserted in the port of each channel, and the valve of each channel must be opened. This requires connection of the cleaning solution injection tube into each channel and a switching operation of the valve of each channel. Procedures for cleaning channels of an endoscope have therefore been complex. With the conventional system as described above, there is an important problem in that incomplete cleaning frequently occurs, especially of the small portions of the valve body of the valve or the portion of the cylinder which is covered with the valve body.

In view of this problem, the present applicant has previously proposed, in Japanese patent application No. 56-111940, a cleaning instrument for cleaning channels of an endoscope which is free from such a problem. According to this instrument, the cleaning solution is supplied through an air/liquid supply cylinder and a suction cylinder formed in a control section of an endoscope so as to allow simultaneous cleaning of the interiors of the channels and the inner surfaces of the cylinders. More specifically, valve bodies inserted in the air/liquid supply cylinder and suction cylinder are pulled out, and adaptors are inserted in the open cylinders. Liquid supply tubes connected to these adaptors are connected to a liquid supply pump. A liquid is supplied from the liquid supply pump to the respective cylinders. The liquid is then flowed from the cylinders to the suction opening and nozzle at the distal end of the endoscope and to the air supply port, liquid supply port and suction port of the connector portion through the liquid supply channel, the air supply channel and the suction channel, respectively, thereby cleaning these channels.

However, the various channels of an endoscope generally have different inner diameters. More specifically, the air supply channel and liquid supply channel generally have small diameters while the suction channel has a large diameter. With one single channel alone, that portion of the channel which extends in the insertion section of the endoscope has a small diameter, and that portion of the channel which extends in the light guide cable has a large diameter. For this reason, when a liquid is supplied from the cylinders to the respective channels, the liquid flows to the channel or channel portion offering the least flow resistance, and a sufficient amount of cleaning solution cannot be flowed to a channel or channel portion offering a larger flow resistance. This results in a problem of incomplete cleaning of the endoscope channels.

SUMMARY OF THE INVENTION

Accordingly, the object of the present invention is to provide a method of cleaning channels of an endoscope, which makes it possible to easily and completely clean the channels and valve cylinders of an endoscope.

According to an aspect of the invention there is provided a method of cleaning the channels of an endoscope, which comprises steps of placing a member in a prescribed position so that liquid may flow between a first end of a suction channel and a nozzle; closing the open end of an air/liquid supply valve cylinder and the open end of a suction valve cylinder; bringing second ends of two of the suction channel, an air supply channel and a liquid supply channel into contact with liquid; and sucking the liquid from the second end of the remaining one of the three channels through the three channels and through the air/liquid supply valve cylinder and the suction valve cylinder, thereby cleaning the interior of these channels and cylinders.

BRIEF DESCRIPTIOIN OF THE DRAWINGS

DETAILED DESCRIPTION OF THE PREFERRED EMBODIMENTS

A few preferred embodiment of the present invention will now be described with reference to the accompanying drawings.

Figure 1:
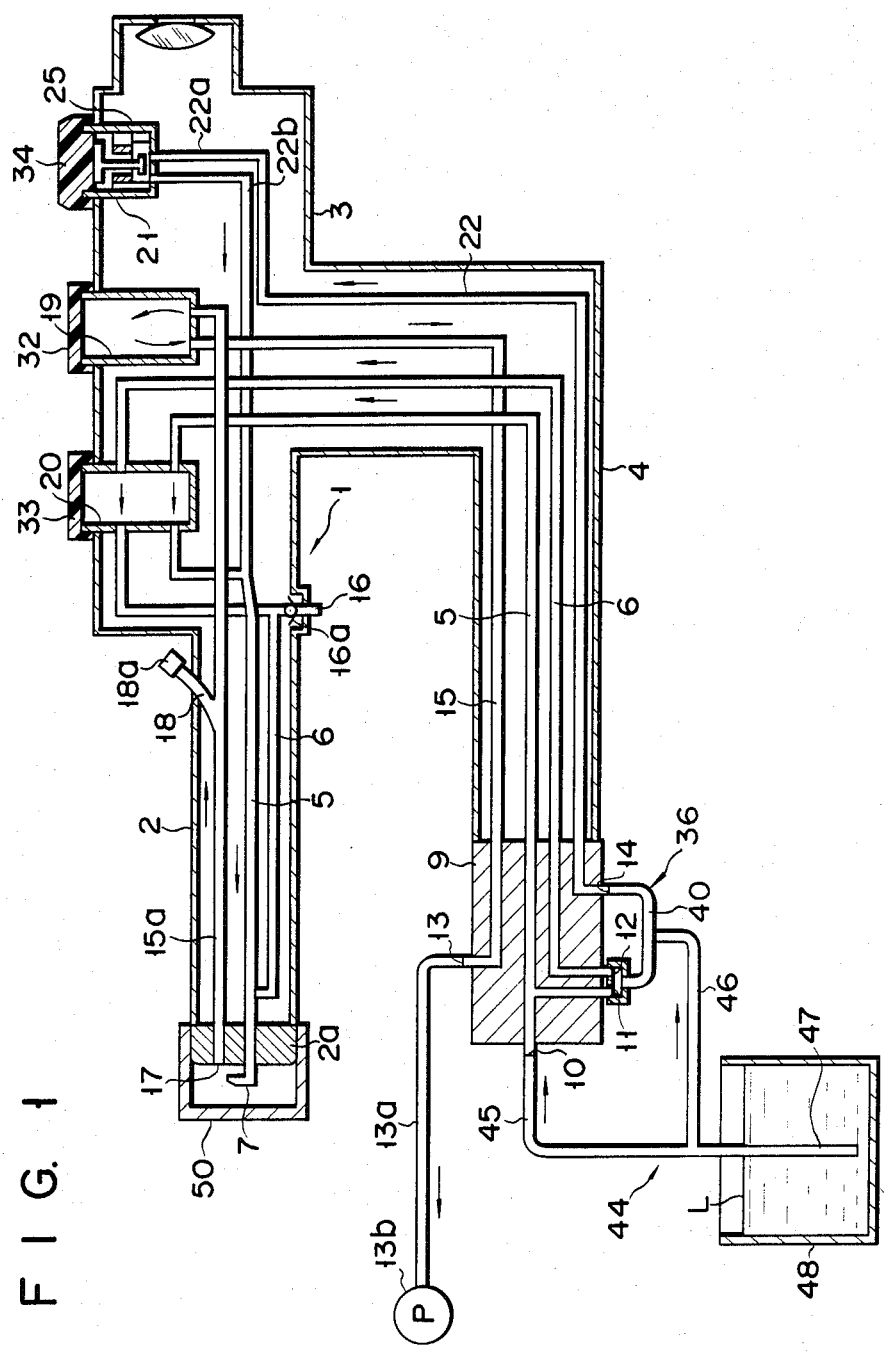
FIG. 1 is a cross-sectional view of an endscope, illustrating how to clean channels by a first method according to the invention.

FIG. 1 is a cross-sectional view of an endoscope 1. The endoscope 1 comprises a control section 3, an insertion section 2 extending from the control section 3 and a light guide cable 4 extending from the control section 3. Various channels (described later) are formed inside the endoscope 1. First, an air supply channel 5 and a liquid supply channel 6 are formed extending through the insertion section 2, the control section 3 and the light guide cable 4. The distal ends of the air supply channel 5 and the liquid supply channel 6 merge to be connected to an air/liquid supply nozzle 7 at the distal end 2a of the insertion section 2. The air/liquid supply nozzle 7 is arranged to face the outer surface of an observation window (not shown) so as to spray air or a liquid thereagainst. The light guide cable 4 has a connector 9 at the free end. The connector 9 has first and second air supply ports 10 and 11 both communicating with the air supply channel 5, a liquid supply port 12 communicating with the liquid supply channel 6, a suction port 13 communicating with a suction channel to be described later, and a gas supply port 14. When the connector 9 is connected to a light source device (not shown), the first air supply port 10 is connected to an air supply pump in the light source device. The second air supply port 11 and the liquid supply port 12 are connected to a liquid supply tank (not shown). The suction port 13 is connected to a suction pump 13b as a vacuum suction unit through a suction tube 13a.

Meanwhile, a suction channel 15 is formed to extend along the entire length of the insertion section 2, the control section 3 and the light guide cable 4. That end portion of the suction channel 15 which is at the side of the insertion section 2 serves as an instrument insertion channel 15a. The distal end of the instrument insertion channel 15a communictes with a suction opening 17 opening to the distal end face of the insertion section 2. The proximal end of the instrument insertion channel 15a opens externally at the control section 3 to form a forceps port 18. The forceps port 18 is closed with a detachable stop 18a. A sub liquid port 16 having a check valve 16a communicates with the liquid supply channel 6.

Figure 2:
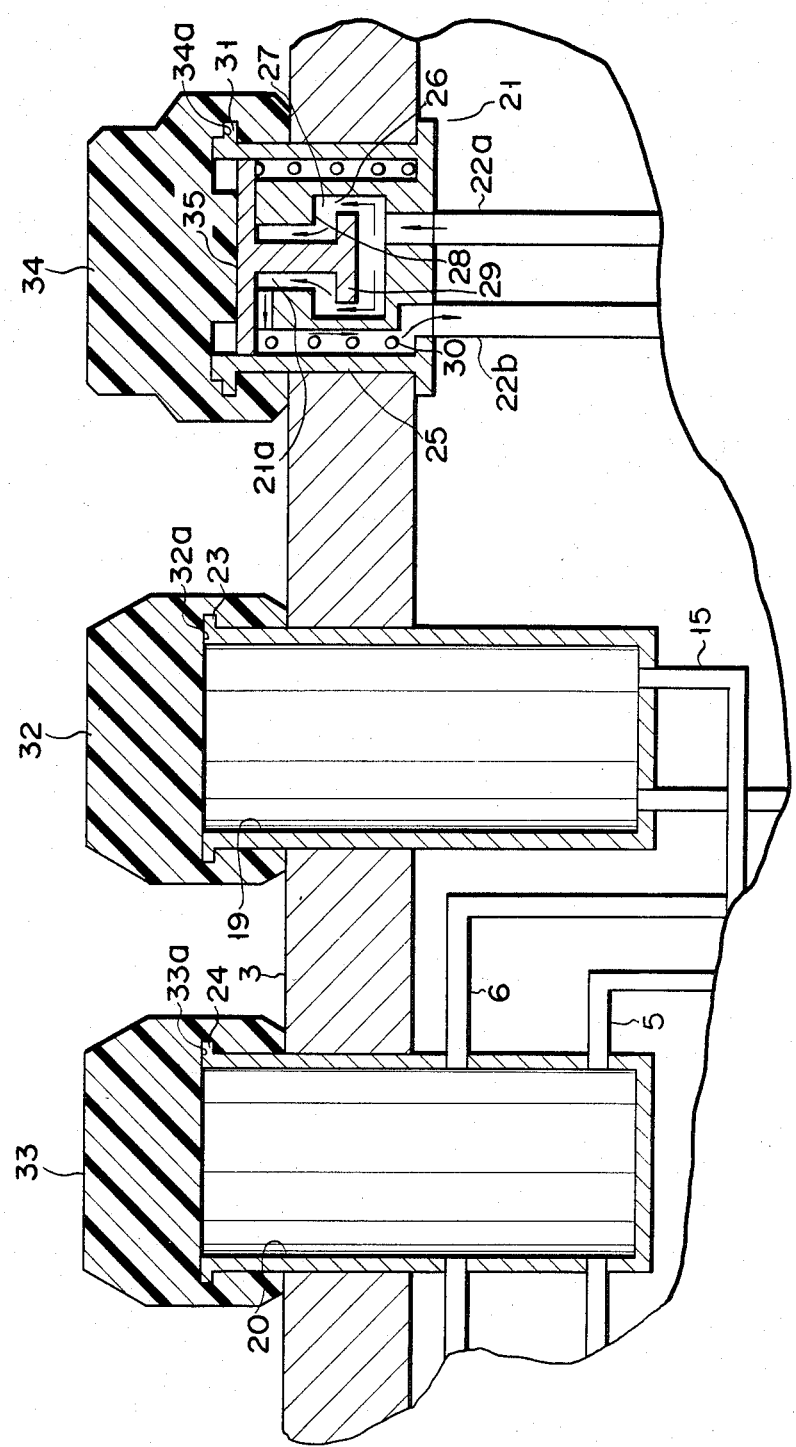
FIG. 2 is an enlarged view of the control section of the endoscope shown in FIG. 1.

The instrument insertion channel 15a is connected to the proximal end of the remaining portion of the suction channel 15 through a suction cylinder, that is, a suction valve cylinder 19. An air/liquid supply cylinder or air/liquid supply valve cylinder 20 is inserted midway along both the air supply channel 5 and the liquid supply channel 6. The valve cylinders 19 and 20 are arranged next to each other at a side surface of the control section 3. The upper ends of the valve cylinders 19 and 20 open to the outside of the control section 3. A gas supply valve 21 is arranged next to the cylinder 19. A gas supply channel 22 is connected to the gas supply valve 21. One end of the gas supply channel 22 is connected to the air supply channel 5 at a position between the air/liquid supply valve cylinder 20 and the air/liquid supply nozzle 7. The other end of the gas supply channel 22 is connected to the gas supply port 14. The valve cylinders 19 and 20 and the gas supply valve 21 have the construction shown in FIG. 2. The suction valve cylinder 19 has a cylindrical shape with a bottom and has a flange 23 formed integrally therewith at its open edge or upper edge. The air/liquid supply valve cylinder 20 similarly has a cylindrical shape with a bottom and has a flange 24 formed integrally therewith at its open edge. The gas supply valve 21 includes a cylinder 25 and a valve mechanism 26 mounted therein. A valve chamber 27 is formed concentrically in the cylinder 25. A valve body 29 which may be brought into contact with a valve seat 28 is arranged inside the valve chamber 27. The valve body 29 is normally biased by a coil spring 30 to be in contact with the valve seat 28, that is, biased in the valve closing direction. Thus, the valve body 29 normally provides a seal in a path 21a connecting an upstream channel portion 22a and a downstream channel portion 22b of the gas supply channel 22. A flange 31 is formed integrally with the open end of the cylinder 25. Stops 32 and 33 are attached to the valve cylinders 19 and 20, respectively, to close their open ends. Engagement grooves 32a and 33a engaging with the flanges 23 and 24 are formed in the inner surfaces of the stops 32 and 33, so that any increase in internal pressure of the cylinders 23 and 24 may not leak outside the stops 32 and 33. A stop 34 is mounted in the cylinder 25 of the gas supply valve 21 to close its open end. A projection 35 projects downward from the center of the stop 34. When the stop 34 is mounted on the cylinder 25, the projection 35 presses the valve body 29 against the biasing force of the coil spring 30, so that the valve body 29 is separated from the valve seat 28 to open the path 21a. An engagement groove 34a is formed in the stop 34 for engagement with the flange 31a for a similar purpose as described above.

Figure 3:
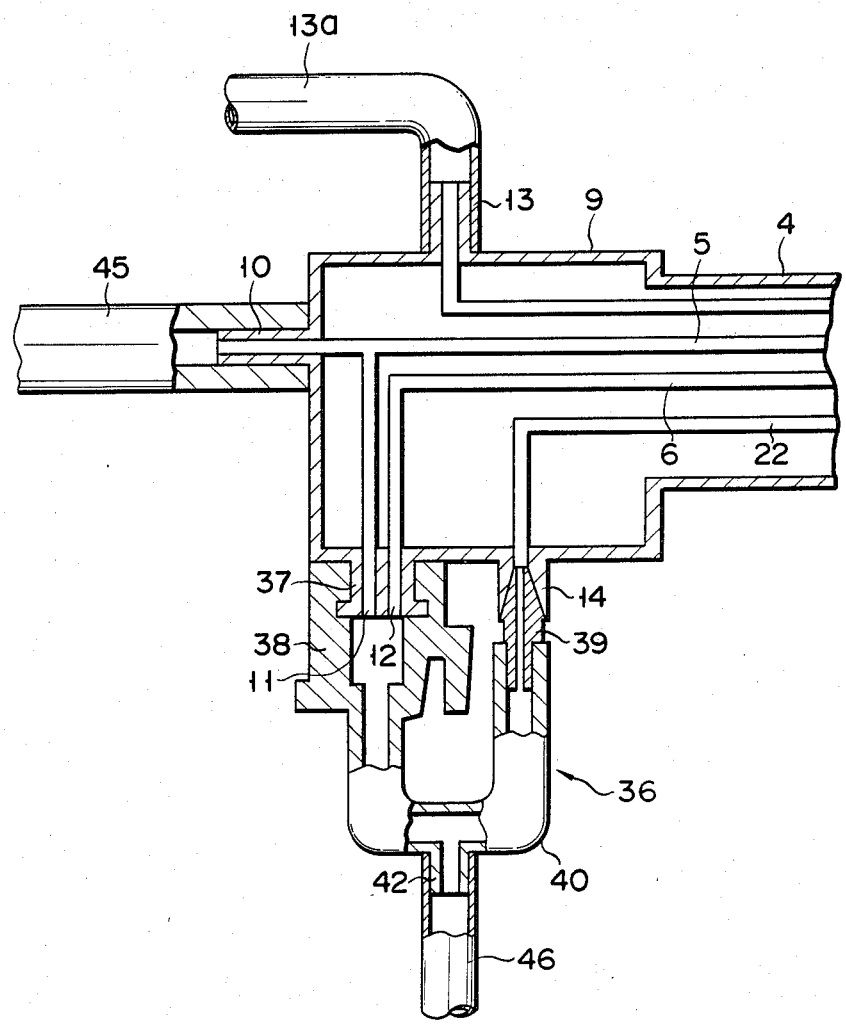
FIG. 3 is an enlarged view of the connector of the endoscope.

The second air supply port 11, the liquid supply port 12 and the gas supply port 14 of the connector 9 are communicated with each other by a channel connector 36, as shown in FIG. 3. The channel connector 36 has a connecting port 38 fitted to an injection nozzle 37 having the second air supply port 11 and liquid supply port 12, an insertion port 39 inserted in the gas supply port 14, and a communication tube 40 connecting the connecting port 38 and the insertion port 39. The communication tube 40 has a connecting portion 42. A liquid supply tube 44 is connected to the connecting portion 42 and the first air supply port 10, repectively (FIG. 1). The liquid supply tube 44 is formed into three portions. A first channel portion 45 of the liquid supply tube 44 is connected to the first air supply port 10, and a second channel portion 46 thereof is connected to the connecting portion 42. A third channel portion 47 of the liquid supply tube 44 is submerged in a liquid L held in a liquid tank 48. A cap 50 is detachably and hermetically mounted at the distal end 2a of the insertion section 2, as shown in FIG. 1. Therefore, the nozzle 7 and the suction opening 17 communicate with each other through the space defined inside the cap 50.

Pistons (not shown) are generally inserted in the suction valve cylinder 19 and the air/liquid supply valve cylinder 20. These pistons serve to allow or block communication between upstream channel portions and downstream channel portions of the air supply channel 5, the liquid supply channel 6 and the suction channel 15, respectively. However, when the stops 32 and 33 are to be mounted on the cylinders 19 and 20, respectively, the pistons are removed first.

The method of cleaning the channels of the endoscope 1 described above will now be described. First, as shown in FIG. 1, the stops 32, 33 and 34 are attached to the cylinders 19, 20 and 25, respectively. At the same time, the suction pump 13b is connected to the suction port 13, while the liquid supply tube 44 is connected to the connecting portion 42 of the first air supply port 10 and the communication tube 40. When the suction pump 13b is operated under this condition, the interior of the suction channel 15 is kept at a negative pressure. Then, since the cap 50 causes communication between the suction opening 17 and the nozzle 7, the interiors of the air supply channel 5, the liquid supply channel 6 and the gas supply channel 22 communicating with the air supply channel 5 are all kept at a negative pressure.

When the respective channels are kept at a negative pressure in this manner, the liquid L in the liquid tank 48 is sucked into the air supply channel 5, the liquid supply channel 6 and the gas supply channel 22 through the first and second air supply ports 10 and 11, the liquid supply port 12 and the gas supply port 14. The liquid L which has flowed into the air supply channel 5 and the liquid supply channel 6 then flows into the space inside the cap 50 through the nozzle 7 via the air/liquid supply valve cylinder 20. Meanwhile, the liquid L which has flowed into the gas supply channel 22 flows into the valve chamber 27 through the upstream channel portion 22a, is vented through the open valve mechanism 26 to the downstream channel portion 22b which communincates with the air supply channel 5 at a point midway therealong, and flows into the space inside the cap 50 through the air supply channel and the air/liquid supply nozzle 7. Therefore, the air supply channel 5, the liquid supply channel 6 and the gas supply channel 22 are cleaned along their entire length. At the same time, the interiors of the air/liquid supply valve cylinder 20 and the gas supply valve 21 are simultaneously cleaned. Since the liquid L flows in a direction so as to flow outward from the nozzle 7, contaminants attached to the nozzle 7 can be exhausted. Since the nozzle 7 has a small diameter, if the liquid L were flowed into the liquid supply channel through the nozzle 7, the flow rate of the liquid L could not be increased and it would be difficult to remove contaminants from the nozzle 7. However, when the liquid L is flowed out from the nozzle 7, the liquid L can be flowed at a high speed and contaminants can be removed with high efficiency.

The liquid L which has flowed into the space inside the cap 50 in this manner then flows into the suction channel 15 through the suction opening 17. The liquid L then flows out from the suction port 13 through the suction valve cylinder 19. Therefore, the suction channel 15 can be cleaned along its entire length, and the interior of the suction valve cylinder 19 can also be cleaned. With such a flow of the liquid L, the interiors of the cylinders 19, 20 and 25 connected to the channels 5, 6, 15, and 22 can be completely cleaned.

In the above description, the liquid is water or a disinfectant. In general, disinfection is performed with a disinfectant. However, the term cleaning used herein includes both washing with water and disinfection or sterilization.

According to the first embodiment, as has been described above, the interiors of the channels are kept at a negative pressure to draw by suction a liquid through those ends of an air supply channel and a liquid supply channel which open at the side of the connector. The liquid which has been drawn by suction in this manner is then exhausted through the nozzle. The liquid flowing out through the nozzle flows into the suction channel through the suction opening and then flows out through that end of the suction channel which opens at the side of the connector portion. Accordingly, various channels and cylinders of the endoscope can be easily and satisfactorily cleaned. Since the liquid is drawn in by vacuum suction, the supply of liquid completely fills all the interior spaces thereof, irrespective of differences in the inner diameters of the various channels and cylinders, thereby ensuring proper cleaning. The method also provides an excellent operability since no special operation is required for cleaning channels and cylinders of the endoscope.

In the first embodiment described above, the liquid supply tube 44 is connected to the air supply port 10 and the communication tube 40 so that the liquid L flows into the channels 5, 6 and 22 from the port 10 and the tube 40. However, the liquid supply tube 44 can alternatively be connected only to the air supply port 10, and the connecting portion 42 of the communication tube 40 can be closed to flow the liquid L into the channels 5, 6 and 22.

Figure 4:
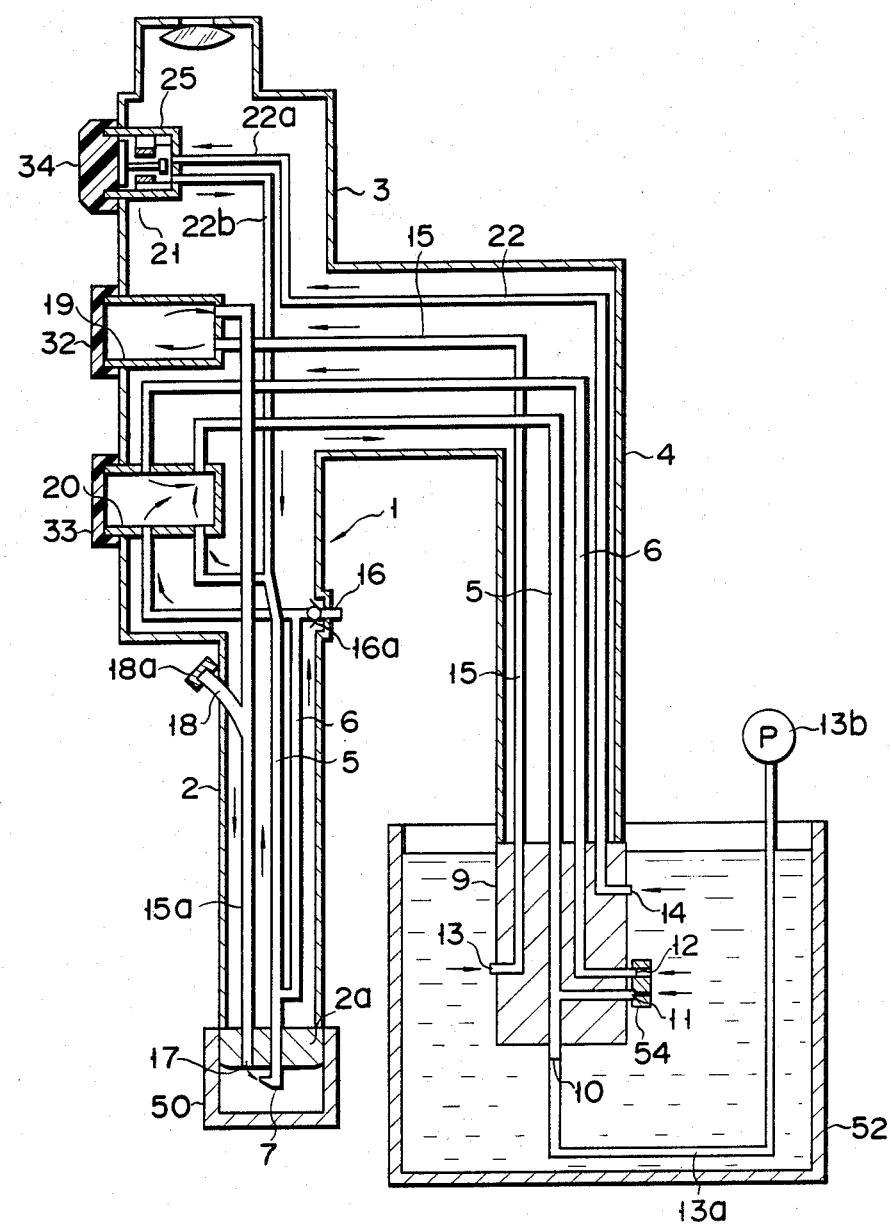
FIG. 4 is a cross-sectional view of the endoscope, showing how to clean the channels by a second method according to the invention.
Figure 5:
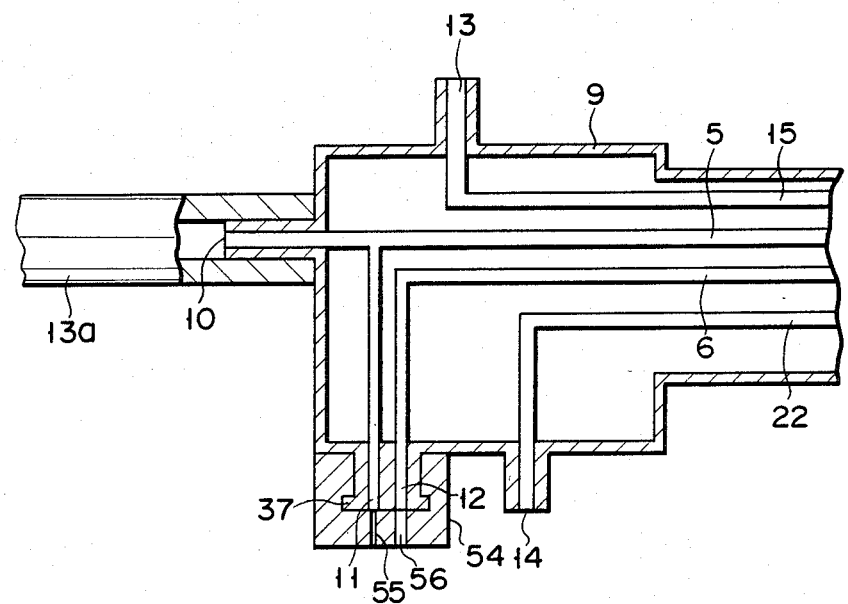
FIG. 5 is an enlarged view of the connector of the endoscope and liquid supply tubes.

FIGS. 4 and 5 show a second embodiment of the present invention. Of the members forming this embodiment, only those which are different from the members consitututing the first embodiment will be described.

In the second embodiment, a connector 9 is submerged in a liquid L held in a container 52. The first air supply port 10 of the connector 9 submerged in liquid L is connected to one end of a suction tube 23a. The other end of the suction tube 13a is guided outside the container 52 and is connected to the suction side of a suction pump 13b. An exhaust tube (not shown) is connected to the delivery side of the suction pump 13b and communicates with a liquid exhaust tank (not shown). A second air supply port 11 and a liquid supply port 12 at the connector 9 open to a connecting portion 37, as shown in FIG. 5. A restriction member 54 is detachably mounted on the connecting portion 37. A small hole 55 communicating with the second air supply port 11, and a communication hole 56 communicating with the liquid supply port 12 are formed in the restriction member 54. The open area of the second air supply port 11 is regulated to be small by means of the small hole 55.

According to the second embodiment, first, as shown in FIG. 4, stops 32, 33 and 34 are atttached to cylinders 19, 20 and 25. At the same time, a stop 18a is mounted on a forceps port 18. The suction tube 13a is connected to the first air supply port 10 of the connector 9, and the connector 9 is submerged in the liquid L. A cap 50 is mounted on the distal end 2a of the insertion section 2. When the suction pump 13b is operated in this state, the upstream channel portion of an air supply channel 5 is kept at a negative pressure. Then, the downstream channel portion of the air supply channel 5 communicating with the upstream channel portion through the cylinder 20, and the upstream and downstream channel portions of a liquid supply channel 6 are kept at a negative pressure. When the air supply channel 5 and the liquid supply channel 6 are kept at a negative pressure along their entire length, a suction channel 15 communicating with a nozzle 7 through a suction opening 17 is kept at a negative pressure along its entire length. At the same time, a gas supply channel 22 communicating with the air supply channel 5 is also kept at a negative pressure along its entire length. When all the channels are kept at a negative pressure in this manner, the liquid L is sucked into the second air supply port 11, the liquid supply port 12, the suction port 13 and the gas supply port 14 at the conector 9 submerged in the liquid L, and flows as indicated by the arrows in FIG. 4. More specifically, the liquid L drawn in through the liquid supply port 12 flows into the air/liquid supply valve cylinder 20 through the upstream channel portion of the liquid supply channel 6, and is then drawn into the upstream channel portion of the air supply channel 5. The liquid L drawn in through the suction port 13 flows into the suction valve cylinder 19 through the upstream channel portion of the suction channel 15, and then flows into the cap 50 through the suction opening 17 via the downstream channel portion 15a. Since the forceps port 18 is closed by the stop 18a at this time, the liquid L does not flow out therethrough. The liquid L flowed into the cap 50 is drawn into the downstream channel portions of the air and liquid supply channels 5 and 6, respectively, through the nozzle 7. The liquid L then flows into the air/liquid supply valve cylinder 20 and is drawn into the upstream channel portion of the air supply channel 5. The liquid L drawn in through the gas supply port 14 flows into the gas supply valve cylinder 25 through an upstream channel portion of the gas supply channel 22 and then flows into a downstream channel portion thereof. Since the downstream channel portion of the gas supply channel 22 communicates with the downstream channel portion of the air supply channel 5, the liquid L from the cylinder 25 flows into the air/liquid supply valve cylinder 20 and is drawn into the upstream channel portion of the air supply channel 5. The liquid L which has passed through the respective channels 5, 6, 15 and 22 and the respective cylinders 19, 20 and 25 flows in the upstream channel portion of the air supply channel 5 and is drawn by the suction pump 13b. The liquid L is also drawn through the second air supply port 11. However, the open area of the second air supply port 11 is regulated to be small by means of the small hole 55 formed in the restriction member 54. Accordingly, the amount of liquid which is drawn through the air supply port 11 is extremely small. The liquid L drawn through the second air supply port 11 flows to the first air supply port 10, as indicated by the arrow shown in FIG. 4.

With the flow of the liquid L described above, the respective channels 5, 6, 15 and 22 can be cleaned along their entire length and at the same time the inner surfaces of the cylinders 19, 20 and 25 can be easily and completely cleaned, as in the first embodiment.

In the second embodiment, the second air supply port 11 can be closed. Alternatively, the second air supply port 11 can be connected to the suction tube 13a as in the case of the first air supply port 10.

Although the first and second embodiments are used in combination with the endoscope 1 having the gas supply valve 21 and gas supply channel 22, the method of cleaning an endoscope according to the present invention can be similarly applied to an endoscope which does not have a gas supply valve 21 or a gas supply channel.

Figure 6:
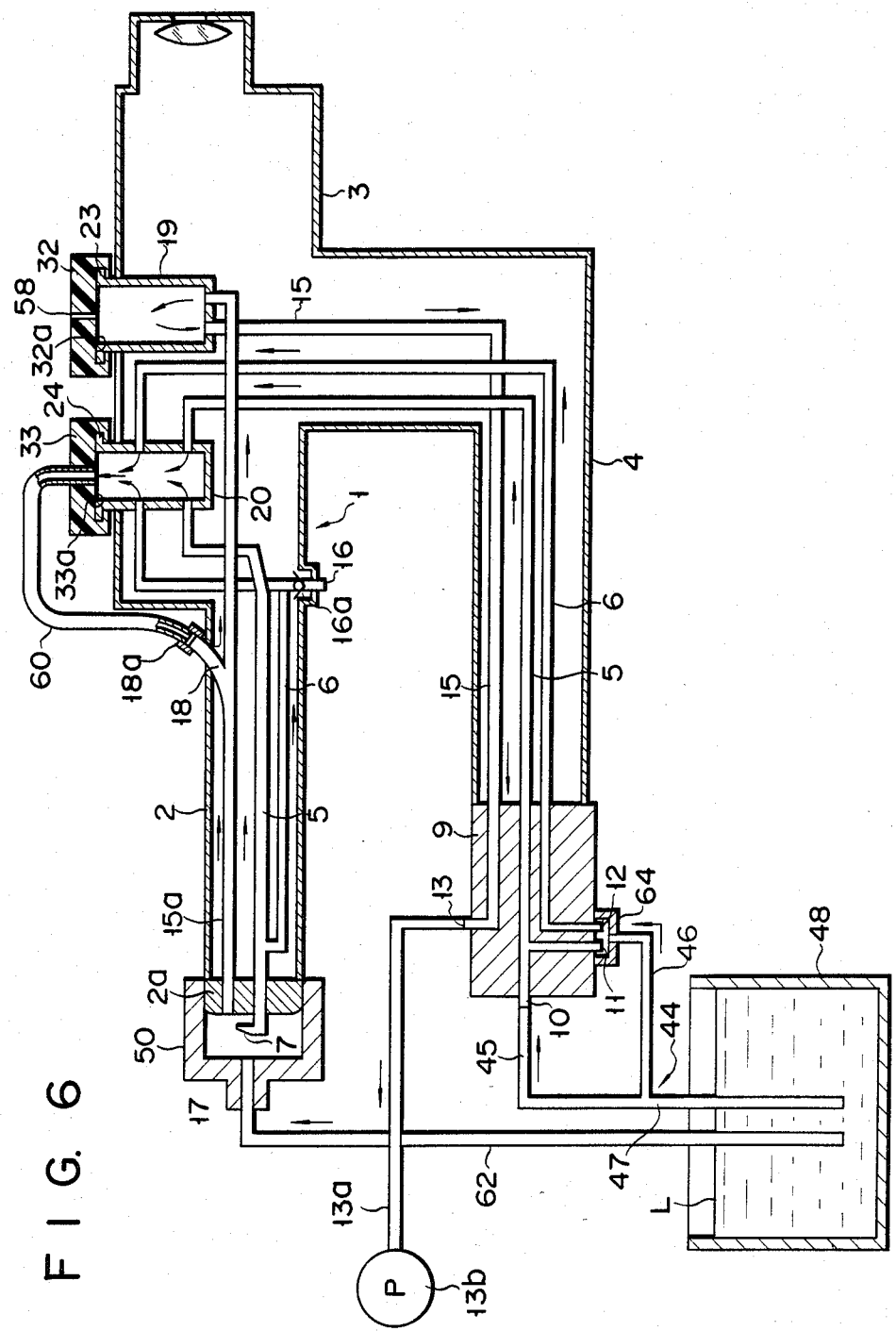
FIG. 6 is a cross-sectional view of another endoscope, showing how to clean channels by a third method according to the invention.

FIG. 6 shows a third embodiment applied to the cleaning of an endoscope which does not have a gas supply valve or a gas supply channel. Of the members forming this embodiment, only those which are different from the members consitituting the first embodiment will be described in detail. In FIG. 6, the same numerals are used to designate like or the same members as those of the first embodiment.

In the third embodiment, a leakage hole 58 is formed in a first stop 32 and communicates with the space inside a suction valve cylinder 19. One end of a communication tube 60 is connected to another stop 33 attached to an air/liquid supply cylinder 20. The other end of the communication tube 60 is connected to a third stop 18a mounted on forceps port 18. Therefore, the forceps port 18 and the air/liquid supply valve cylinder 20 are communicated with each other through the communication tube 60. One end of a liquid supply tube 62 is connected to a cap 50. The other end of the liquid supply tube 62 is guided to a liquid tank 48 and is submerged in a liquid L held therein. A first channel portion 45 of a liquid supply tube 44 is connected to a first air supply port 10, and a connecting port 64 is connected to the terminal end of the second channel portion 46 of the liquid supply tube 44. A connecting port 64 is fitted on a connector to which a second air supply port 11 and a liquid supply port 12 open. Therefore, the second air supply port 11 and the liquid supply port 12 communicate with each other through the internal space of the connecting port 64. The third channel portion 47 of the liquid supply tube 44 is guided to a liquid supply tank 48, and its terminal end is submerged in liquid L.

According to the third embodiemnt, first the stops 32, 33 and 18a are mounted on the cylinder 19, the cylinder 20 and the forceps port 18, respectively, as shown in FIG. 6. Then, the air/liquid supply valve cylinder 20 and the forceps port 18 are connected by the communication tube 60. The cap 50 and the liquid supply tube 62 are attached to the distal end of an insertion section 2. The second liquid supply tube 44 is connected to the first and second air supply ports 10 and 11 and to the liquid supply port 12 of a connector 9. When the suction pump 13b is operated in this state, the suction force serves to keep the suction channel 15 at a negative pressure along its entire length. When the suction channel 15 is kept at a negative pressure, the interior of the air/liquid supply valve cylinder 20 is also kept at a negative pressure through the communication tube 60 connected to the forceps port 18. Therefore, the air supply channel 5 and the liquid supply channel 6 connected to the cylinder 20 are also kept at a negative pressure along their entire length. When the channels 5, 6 and 15 are all kept at a negative pressure along their entire length in this manner, the liquid L in the liquid supply tank 48 is sucked into the channels 5, 6 and 15 from both the liquid supply tubes 44 and 62, as indicated by the arrows shown in FIG. 6. Thus, the liquid L flows from the liquid supply tube 62 into downstream channel portions of the air supply channel 5, the liquid supply channel 6 and the suction channel 15 through the nozzle 7 and the suction opening 17 via the space inside the cap 50. The liquid L also flows from the liquid supply tube 44 into the upstream channel portions of the air supply channel 5 and the liquid supply channel 6 through the first and second air supply ports 10 and 11 and the liquid supply port 12. The liquid L which has flowed into the upstream channel portions of the supply channels 5 and 6 and that which has flowed into downstream channel portions thereof are injected into the air/liquid supply valve cylinder 20 to clean its inner surface, and then the liquid L flows into the downstream channel portion of the suction channel 15 where it merges with the liquid L which has flowed in through the suction opening 17. The liquid L which flows into the downstream channel portion of the suction channel 15 is injected into the suction valve cylinder 19, is returned into the upstream channel portion of the suction channel, flows out through the suction port 13, and is exhausted through the exhaust side of the suction pump 13b. Upon such flow of the liquid L, the channels 5, 6 and 15 can be cleaned along their entire length, and the interiors of the cylinders 19 and 20 can be cleaned simultaneously.

Since the leakage hole 58 is formed in the stop 32 mounted on the suction valve cylinder 19, the external air is drawn in through the leakage hole. Accordingly, when the size of the leakage hole 58 is suitably changed, the negative pressure generated in the suction channel 15 can be controlled. Therefore, the amount of liquid L which flows into the suction channel 15 from the liquid supply tube 62 can be adjusted. In other words, the amount of liquid L which flows into the channels 5, 6 and 15 can be adjusted in accordance with their diameters.

In the third embodiment, the suction tube 13a can be connected to the cap 50, and the liquid supply tube 62 can be connected to the suction port 13 so as to release the liquid L. The suction tube 13a can be connected to the first and air supply ports 10 and 11 and the second liquid supply tube 44 can be connected to the suction port 13 so as to release the liquid L. In other words, if a suction force is applied through at least one of the suction port 13, the suction opening 17 and the first and second air supply ports 10 and 11, while the liquid L flows in through the remaining ones thereof, the channels 5, 6 and 15 and the cylinders 19 and 20 can be simultaneously cleaned.

The present invention is not limited to the embodiments described above. For example, the present invention can also be similarly applied to an endoscope 1 in which an air supply channel 5 and a liquid supply channel 6 communicate with separate nozzles 7 at a distal end 2a of an insertion section 2.

The suction pump as a means for drawing a liquid by vacuum suction can be a piston-type syringe.

What is claimed is:

1. A method of cleaning channels of an endoscope which includes a control section, an insertion section extending from the control section and having a nozzle at its distal end, a light guide cable extending from the control section and having a connector at its distal end, an air supply channel extending in the endoscope and having one end communicating with the nozzle and the other end opening to the connector, a liquid supply channel extending in the endoscope and having one end communicating with the nozzle and the other end opening to the connector, a suction channel extending in the endoscope and having one end opening to the distal end of the insertion section and the other end opening to the connector, an air/liquid supply valve cylinder arranged in the control section to communicate with the air supply channel and liquid supply channel and having one end opening to the outside of the control section, and a suction valve cylinder arranged in the control section to communicate with the suction channel and having one end opening to the outside of the control section; said method comprising:

a first step of placing a confining member in a prescribed position so that liquid is confined to flow between said one end of said suction channel and said nozzle;

a second step of closing the open end of said air/liquid supply valve cylinder and the open end of said suction valve cylinder;

a third step of bringing the other ends of two of said suction channel, air supply channel and liquid supply channel into contact with liquid; and a fourth step of sucking the liquid from the other end of the remaining one of said three channels through said three channels, said air/liquid supply valve cylinder and said suction valve cylinder, thereby cleaning the interior of the channels and cylinders.

2. A method according to claim 1, wherein the other ends of said air supply channel and liquid supply channel are in contact with the liquid, and the liquid is sucked from the other end of said suction channel.

3. A method according to claim 1, wherein said fourth step includes connecting the other end of the remaining one of said three channels to a sucking means, and said third step includes connecting the other ends of the other two of said three channels to a tank filled with liquid by liquid supply tubes to suck the liquid from the remaining one of said three channels.

4. A method according to claim 1, wherein said fourth step includes connecting the other end of the remaining one of said three channels to a suction means, and said third step includes submerging said connector in the liquid.

5. A method according to claim 1, wherein the other ends of said liquid supply channel and suction channel are put into contact with the liquid, and the liquid is sucked from the other end of said air supply channel.

6. A method according to claim 1, wherein said third step includes bringing said one end of said suction channel and said nozzle into contact with said liquid and connecting said suction channel to said air/liquid supply valve cylinder through a communication tube.

* * * * *

UNITED STATES PATENT AND TRADEMARK OFFICE
CERTIFICATE OF CORRECTION

PATENT NO. : 4,526,622
DATED : July 2, 1985
INVENTOR(S) : Takamura, et al

It is certified that error appears in the above-identified patent and that said Letters Patent are hereby corrected as shown below:

Title page, Item [30] should read as follows:

-- Foreign Application Priority Data

Apr. 15, 1983 [JP] Japan ................58-66798

Apr. 25, 1983 [JP] Japan ................58-72521

Apr. 27, 1983 [JP] Japan ................58-74773 --

Signed and Sealed this

Twenty-fifth Day of February 1986

[SEAL]

Attest:

Attesting Officer

DONALD J. QUIGG

Commissioner of Patents and Trademarks